United States Patent
Bader

[11] Patent Number: 5,817,041
[45] Date of Patent: Oct. 6, 1998

[54] RIGID LOWER-LIMB ORTHOTIC

[76] Inventor: Wade Bader, 13711 N. Dale Mabry, Tampa, Fla. 33618

[21] Appl. No.: 844,579

[22] Filed: Apr. 21, 1997

[51] Int. Cl.⁶ .................................. A61F 5/00; A61F 5/37
[52] U.S. Cl. ............................... 602/23; 602/62; 128/882
[58] Field of Search ..................... 602/5–8, 23, 27–29; 128/882

[56] References Cited

U.S. PATENT DOCUMENTS

| | | | |
|---|---|---|---|
| 3,916,886 | 11/1975 | Rogers | 602/28 |
| 4,161,175 | 7/1979 | Bentile | 602/6 |
| 4,641,639 | 2/1987 | Padilla | 602/23 |
| 4,834,078 | 5/1989 | Biedermann | 602/27 |
| 5,154,690 | 10/1992 | Shiono | 602/26 X |
| 5,226,875 | 7/1993 | Johnson | 602/27 |
| 5,605,535 | 2/1997 | Lepage | 602/27 |

FOREIGN PATENT DOCUMENTS

2168610  6/1986  United Kingdom ..................... 602/28

*Primary Examiner*—Richard J. Apley
*Assistant Examiner*—Denise Pothier

[57] ABSTRACT

A lower limb orthotic comprising a foot orthotic, a pair of lateral supporting members, a detached or removeable anterior support member, a posterior support member, and strips of composite materials to resist plantar flexion, dorsiflexion and various of movements of the foot and ankle. The lateral supporting members further having strips of composite materials having fibers orientation substantially parallel to the length wise axis of the lateral supporting members. The foot orthotic and posterior supporting member further have composite strips extending across the bottom portion of the foot orthotic and rear side of the posterior supporting member respectively.

4 Claims, 8 Drawing Sheets

FIGURE 8
SUPINATION & PRONATION

RIGID LOWER-LIMB ORTHOTIC

BACKGROUND

1. Field of the Invention:

Generally, this invention is directed towards improved orthosis. More specifically, this invention is directed towards improved lower limb orthosis. Even more specifically, this invention provides a rigid lower limb orthotic using strategically placed high-tech composite materials that impedes plantar flexion and dorsiflexion movements and aligns and supports the lower limbs and joints.

2. Description of the Prior Art:

One of the largest classes of orthosis are categorized in what are called stabilizing or supportive orthosis. These orthosis permit the patient to control an otherwise uncontrollable segment or an entire limb. They stabilize joints by preventing unwanted motion, and they stabilize limbs for weight-bearing. Such devices are used in the presence of painful joints, structural inadequacies produced by a variety of diseases, traumatic incidents, genital abnormalities, flaccid paralysis, and spastic paralysis.

Some of the terms related to movements of the foot and ankle are an axis, or axis of rotation, which is a line about which a revolving body turns. The axis does not necessarily pass through the revolving body. Dorsiflexion and plantar flexion refer to rotation about a horizontal axis that is perpendicular to the sagittal plane. Abduction and adduction refer to rotation about a vertical axis. Supination and pronation refer to rotation about a horizontal axis that is perpendicular to the frontal plane. Of course the foot and ankle are not simple rotations in one plane, but are compound movements made up of components of motion in various planes occurring simultaneously. In compound motions, the projection of movement in the sagittal plane corresponds to the component of motion defined as dorsiflexion and plantar flexion. The projection in the Horizontal plane corresponds to the motion defined as abduction-adduction. The projection in the frontal plane corresponds to the motion defined as supination-pronation. For purposes of brevity, it is often preferable to use the term describing the most dominant component of movement alone, and this is acceptable as long as it does not lead to confusion.

One of the primary functions of lower limb orthosis is to control the alignment and motion of the lower limbs of a patient, more specifically the joints. Over the years, prefabricated metal components were used almost exclusively in the production and manufacture of lower limb orthosis. The evolution of these components and designs have changed with the introduction of different materials such as plastic and other polymer materials.

Metals such as aluminum and stainless steel are primarily used to give structural support and elasticity to the orthosis. A problem with using metal components, especially for applications requiring resiliency, is that metals tend to develop metal fatigue during use and break over time. This lack of durability makes metal components obsolete when compared to today's high-tech component materials. Another problem with using metal components is the additional weight added to the orthotic making the orthotic difficult and cumbersome to use. Furthermore, metal components tend to be cosmetically unattractive and thus discourage patients from using the orthotics in the prescribed fashion.

Today, many manufacturers have taken advantage of using high-tech composite materials such as graphite and the like for the construction of orthotics. Even though these high-tech materials initially costs more to use, their durability and all around advantages make them a much better investment then metal and plastic materials.

An advantage in using components such as graphite fibrous materials with the construction of orthotics, is that composite fibers are light weight, resilient, strong, rigid and durable. Additionally, many of the above parameters can be adjusted depending upon the number of fibers used and the fiber orientation of the composite materials. The resiliency of composite fibers allows orthotics to flex many times more than materials such as metals and plastic without damage or abatement in the structural integrity of the orthotic.

Several approaches have been provided for the construction of lower limb orthotics, in U.S. Pat. No. 5,176,623, "An orthopedic brace for articulated joints of the human body and the members of the body joined by such joints is comprised of support members for securement to respective body members on opposite sides of the joint and a hinge assembly connection the support members and providing an axis of oscillation aligned with the axis of articulation of the joint; the hinge assembly including retention surfaces on one hinge member and a locking device on another hinge member cooperative with the retention surfaces for supporting the joint and the associated body members in any one of plurality of fixed angle positions during normal activity' for quick release from the fixed position to a free-floating condition to enable the wearer to periodically engage the therapeutic and/or rehabilitative exercise of the joint without having to remove the brace; and for quick and facile return to the selected fixed angle position without having to engage in tedious readjustment of the brace following exercise. In the preferred embodiment illustrated and described, the appliance comprises a lower leg and ankle walker for holding the foot and ankle in any one of a plurality of fixed positions and for release from accommodate rehabilitative articulation of the ankle in both dorsiflexion and plantar flexion."

In the art described by U.S. Pat. No. 5,269,748, "A therapeutic leg and foot device comprising an L-shaped member having an elongated channel-like portion adapted to fit the posterior region of the lower leg and a foot portion extending integrally at right angles therefrom. The integral connection is curved to avoid contact with the patient's heel when the device is in place. The channel shape flattens out at the curved portion and is narrowed to promote the required flexing at this point. The device is constructed of resilient transparent acrylic plastic material which is resilient under a stress load but has sufficient rigidity to maintain a bed patient's foot in properly disposed position to prevent bed sores or drop foot. However, when used in the correction of drop foot, the foot portion is flexed away from the perpendicular to an obtuse angle with the leg portion to conform to the deformity. In this position, the device exerts a 30 to 50 lb. pressure on the foot area to bias the foot back into normal position. There is also an equal amount of pressure or counter force on the lateral arch to correct outward turning of a foot usually associated with a foot drop deformity. This rigid flexibility also permits its use as an abulation aid in gait training. The device is provided with releasable means for securing to the patient's foot. Attachments may be made for preventing undesirable rotation of the leg; for making the device rigid to maintain the immobility of the foot and heel; and for maintaining the bed sheets and blankets in spaced relation to the patient's toes."

In the art described and taught by U.S. Pat. No. 5,372,576, "A therapeutic device for attachment to the foot and leg of a user for alleviating and correcting foot deformities, and for maintaining the foot in a fixed, stable, yet comfortable position following surgery or other medical procedure performed on the foot. The device comprises a leg engaging portion, a foot supporting portion and a heel portion which interconnects and advantageously is integral with the leg and foot portions. The heel portion has an inner and an outer surface and a curvature such that the inner surface of the heel portion can be positioned in sufficient spaced relation to the heel of a user to prevent contact between the inner surface of the heel portion and the heel of the user thereby to eliminate any chafing, or abrasive contact, or decubitus or pain-inducing pressure between the heel of the user and the inner surface of the heel portion. The side margins of the heel portion are adapted to receive releasable fastening members for engaging the foot of a user whereby the inner surface of the heel portion will be maintained in a stable, fixed position in spaced relation to the heel of a user. A one-piece liner is secured to the inside of the device which acts to provide both optimum comfort to the user and to aid in maintaining the foot of a user in the stable, fixed position established by the releasable fastenings carried on the side margins of the heel portion."

In U.S. Pat. No. 5,330,419, "An orthopedic ankle brace is provided having a pliant boot that surrounds the ankle joint, as well as the foot and lower leg in the region thereof. The boot may incorporate straps for applying compression to the ankle joint. Attached to the boot are a pair of adjustable tension straps vertically disposed about the ankle joint for restricting the mobility thereof. Integral with the boot are a pair of stiffening members positioned about the ankle joint to cooperate with the tension straps in the performance of their mobility restricting function. Further provided integral with the boot are retention members that isolate the malleoli from the stiffening members for the comfort of the wearer. Finally, one or more retention straps are provided to maintain the stability of the brace."

While some of the prior art may contain some similarities relating to the present invention, none of them teach, suggest or include all of the advantages and unique features of the lower limb orthotic as the invention disclosed hereinafter.

SUMMARY

The present invention is directed towards an improved lower limb orthotic having many structural advantages over the prior art. The present invention shows a lower limb orthotic having a pair of lateral supporting members extending vertical at the sides of a patient's calf muscle. At the top region of the lateral supporting members is an anterior support member that wraps around the knee portion of a patient's leg, but is not attached to the orthotic. Also, at the top region is a posterior support member to wrap around the person's calf muscle. The bottom region of the orthotic shows a foot orthotic having a heel portion and a frontal portion. A pair of lateral walls extend upwardly from the foot orthotic to resist any dorsiflexion or plantar flexion movements. There are a number of composite strips that are incorporated into the orthotic and strategically placed at high stress points to further add to the structural integrity. The fiber orientation of these composite strips further adds to the structural integrity and durability of the orthotic.

Accordingly, it is an object of this invention to provide a lower limb orthotic that resist plantar flexion, dorsiflexion, and further resist any varus or valgus deviation of the hind foot and ankle, stabilize the subtalar joint, and to hold the foot in a predetermined position.

Another object of this invention is to provide a lower limb orthotic having a posterior support member that will wrap around the person's calf muscle and secure the orthotic to the lower limb.

Still another object of this invention is to provide a lower limb orthotic having an anterior supporting member that will wrap around a person's knee region and further secure the orthotic to the person's lower limb.

Still yet a another object of this invention is to provide a lower limb orthotic having a pair of lateral supporting members that engage the sides of a person's calf muscles in the vertical length wise direction.

A further object of this invention is to provide a foot orthotic that is an integral part of the orthotic. The foot orthotic contains a heel portion, a frontal portion, and a pair of upwardly extending side walls that resist any dorsiflexion or plantar flexion movements.

Still a further object of this invention is to provide a continuous strip of composite material throughout the lower limb orthotic such that there are no locations in the orthotic having abrupt endings.

Other objects and a fuller understanding of the invention will become apparent from reading the following detailed description of a preferred embodiment in conjunction with the accompanying drawings.

BRIEF DESCRIPTION OF THE DRAWINGS

This invention, together with other objects, features, aspects and advantages thereof, will be more clearly understood from the following description, considered in conjunction with the accompanying drawings.

Eight sheets of drawings are furnished, sheet one contains FIG. 1, sheet two contains FIG. 2, sheet three contains FIG. 3, sheet four contains FIG. 4, sheet five contains FIG. 5, sheet six contains FIG. 6, sheet seven contains FIG. 7, and sheet eight contains FIG. 8.

DESCRIPTION OF THE PREFERRED EMBODIMENTS

Figure 1:
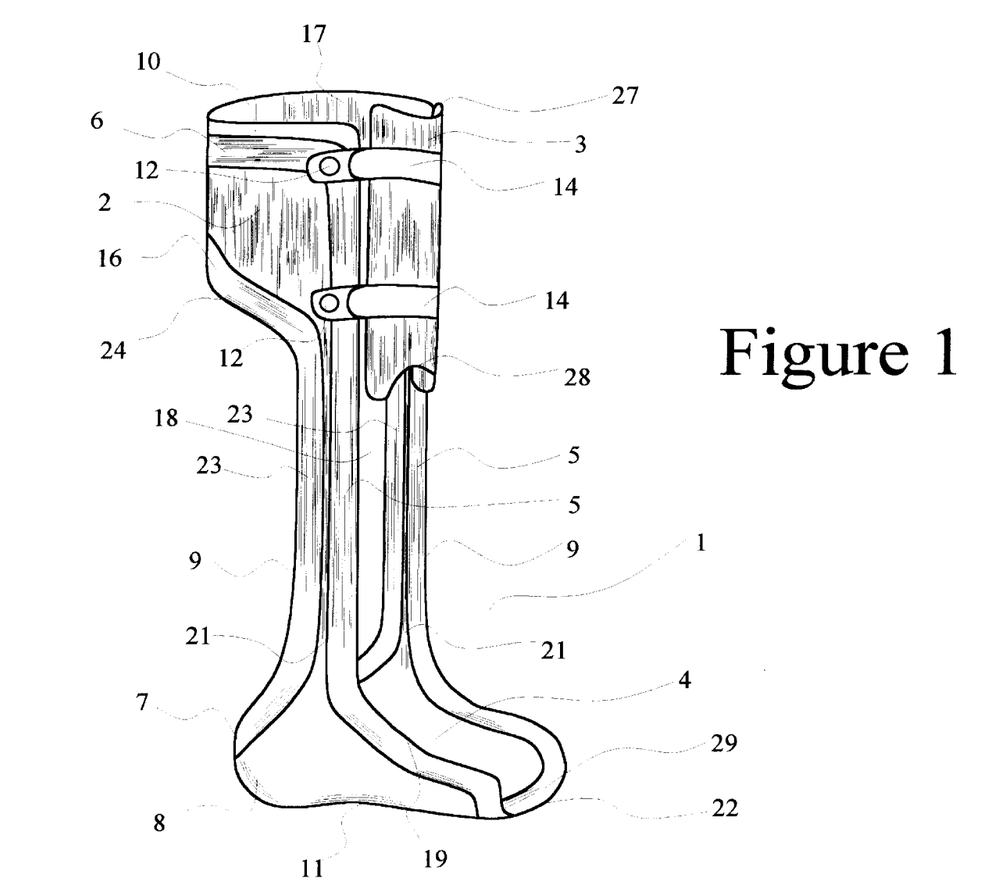
FIG. 1 is an perspective view of the invention showing the anterior upper support member, the posterior support member, the lateral supporting members, and the foot orthotic.
Figure 2:
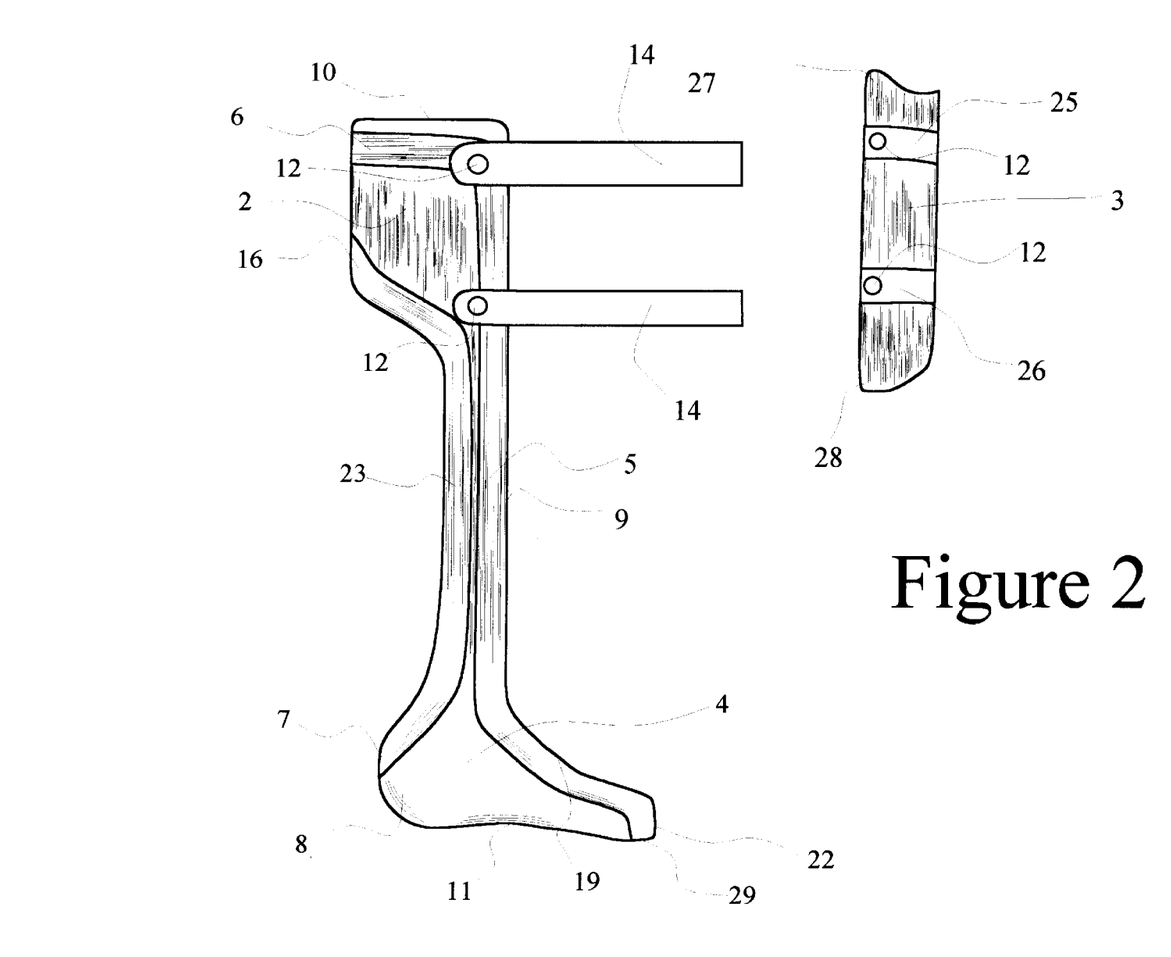
FIG. 2 shows a side, perspective view of the invention displaying the lateral supporting members, the foot orthotic, and the detached anterior upper support member.

Referring now to FIG. 1, a lower limb orthotic for supporting and aligning the lower limbs of a patient referred to generally by reference numeral 1. The lower limb orthotic 1 generally comprising of an anterior upper support member 3, a posterior upper support member 2, a pair of lateral supporting members 9, and a foot orthotic 4.

In the Figures, lateral supporting members 9 are made primarily of vertical strips 5 and 23 of composite materials such as graphite with resin hardening ingredients impregnated therein. The composite materials are generally comprised of a multiplicity individual graphite fibers. Typically, a braided rope of composite material is used to expedite the construction process whereby the individual graphite fibers are substantially aligned with the lateral supporting member 9 in an axis stemming from the top edge 10 to the bottom edge 11 of the orthotic 1. The fiber orientation of the braided graphite rope is crucial to the durability and strength of the orthotic 1. It should be noted that other fibrous composite materials such as Kevlar could possibly be substituted for the graphite in future applications.

At the upper region of the orthotic 1, an anterior support member 3 is shown which wraps around the knee portion of the patient. The anterior support member 3 is attached to the posterior support member 2 by a plurality of straps 14. It is noticed in the figure that a pair a strips of composite material 6 and 16 connect are connected to vertical composite strips 5 and 23 and loop across the posterior support member 3. These strip 6 and 16 for give additional support to the structural integrity of the orthotic 1 and prevent cracks from forming. The strip 6 extends towards the top edge 10, and strip 16 wraps around the lower edge 24. It should also be observed that the strips 6 and 16 are an integral part of the vertical strips 5 and 23 thereby eliminating any abrupt endings in the vertical composite strips. It has been found that cracks tend to emerge from abrupt endings in the composite strips, thus the composite strips 6 and 16 prevent crack formation as well as increases the structural integrity of the orthotic 1. At the anterior region of the posterior support member 2, there is an opening or slot 17 having a hook and loop type of strap 14 crossing thereover. The strap 14 is typically affixed to the posterior support member 2 via bolts 12. Below the posterior support member 2 is another opening or slot 18 which extends downwardly to the foot orthotic 4.

Figure 3:
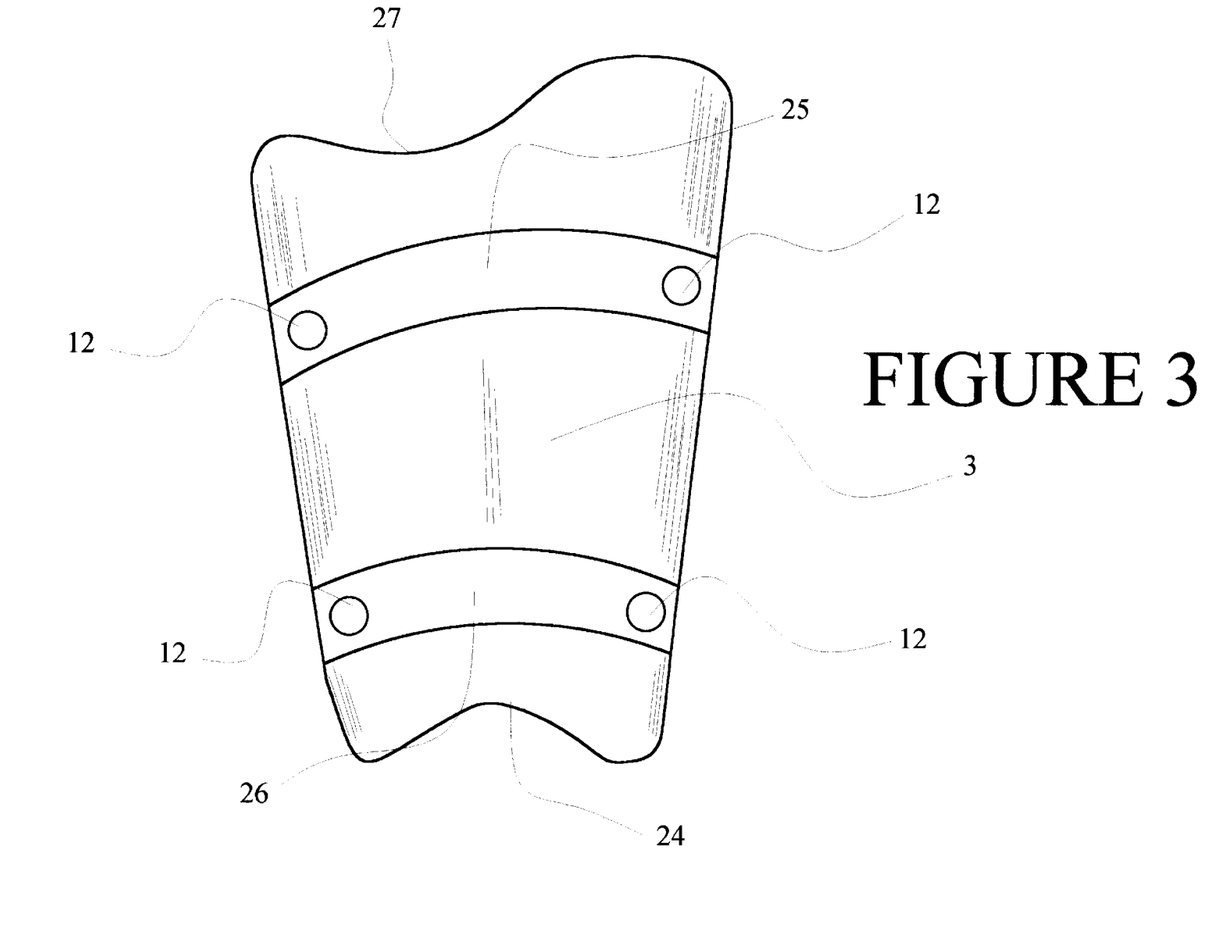
FIG. 3 is a frontal view of the detached anterior upper support member.
Figure 4:
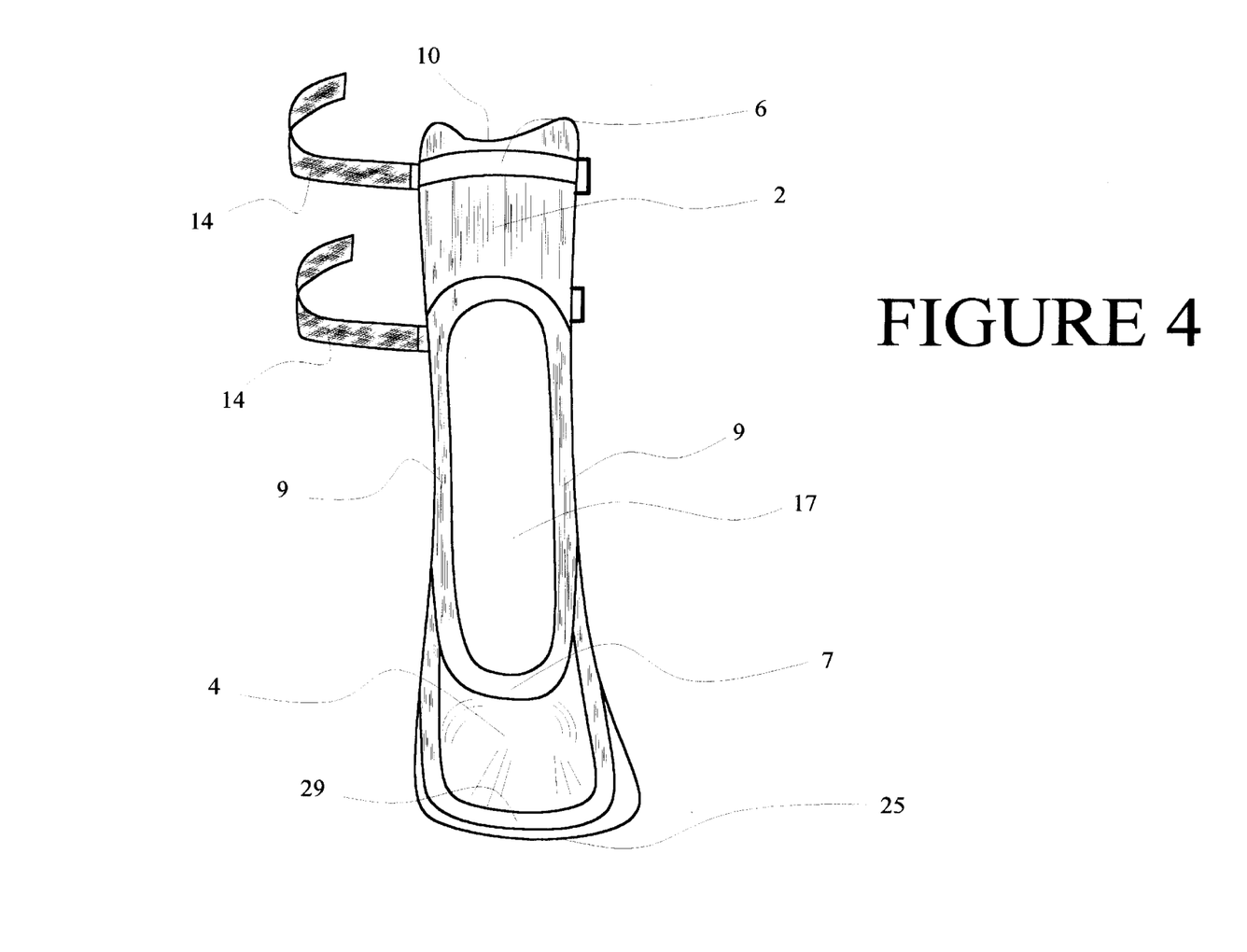
FIG. 4 is a front view of the invention without the anterior upper support member.

The detached anterior support member 3 contains two strips 25 and 26 that are affixed thereto via bolts 12. The strip 25 is affixed at the upper edge 27 of member 3 and the strip 26 is affixed at the lower edge 28 of member 3.

At the lower region of the orthotic 1 is a foot orthotic 4 affixed to the bottom ends 21 of the lateral supporting member 9. The foot orthotic 4 generally comprises of a heel portion 8, lateral walls 19, and a frontal region 22. The lateral walls 19 serve to greatly resist dorsiflexion and plantar flexion movements in the ankle portion of the patient. At the bottom portion of the foot orthotic 4 are a pair of strips 7 and 29 that are integrally connected to strips 23 and 5 respectively, and wrap around the bottom portion of the orthotic 4. The strip 29 is position towards the frontal portion 22, and strip 7 is towards the heel portion 8. The bottom composite strip 29 greatly increases the structural strength of the lateral walls 19 that are responsible for resisting plantar flexion and dorsiflexion movements. Similarly, as with the anterior strips 6 and 16, the bottom composite strips 7 and 29 serve to eliminate any abrupt endings to the lateral composite strips 5 and 23 thereby preventing crack formations. This strategic placement of the composite fibers aligns the individual fibers along with the lateral walls 19 whereby the fiber orientation is more directly aligned parallel to plantar flexion and dorsiflexion movements.

To construct the lower limb orthotic 1, a positive cast is made of the patients lower limb. At least one sleeve of fabric material is then slid over the positive cast. Normally, at least one layer of graphite material is placed throughout the orthotic for increased strength and durability. Strips 5 and 23 of composite fiber material comprising a multiplicity of individual fibers are placed along the lateral supporting members 9, across the posterior support member 2, and across the bottom of the foot orthotic 4. The strips 6 and 16 are positioned in close proximity to edges 10 and 24 respectively. The fiber orientation in the lateral supporting member region are aligned parallel to the axis formed between the top edge 10 and bottom edge 11. The composite fiber strips 7 and 29 in the foot orthotic region 4 are angled towards the heel and frontal portion 22 respectively. Note, this strip of composite materials used is usually in the form of a braided rope with a hollow interior that is sent from the manufacturer. It should be noted that the composite strip normally used is that of a single unit but possibly could be made of multiple strips of composite materials. Normally, the composite strips are all integral parts of each other thereby eliminating any abrupt endings in the strips. Note for additional strength, or stiffness, additional composite strips can be applied on top of the first composite strips.

A bag is placed over the entire mold and resin hardening ingredients are impregnated into the first material layer, the composite fibers, and the second material layer where they are allowed to cure. Next, the lower limb orthotic 1 is removed from the positive cast mold and trimmed whereby the posterior support member 2, foot orthotic 4 and other components are all formed accordingly. Note, in the lateral supporting member region 9, most excess materials (i.e. first and second material layers) are trimmed off thereby leaving a relatively thin lateral supporting member made primarily of composite strips 5 and 23. It becomes economically advantages to use strips of composite materials strategically placed in the orthotic because hardly any excess composite materials are trimmed off, thus waste is kept to a minimum.

A common flexible calf strap 14 is attached to the posterior support member 2 and secured via bolts 12. The anterior support member 3 also contains straps 25 and 26 that are affixed to the front surface. The straps 14 contains hook and loop material affixed to their surfaces thereby making easy connections to one another.

Figure 5:
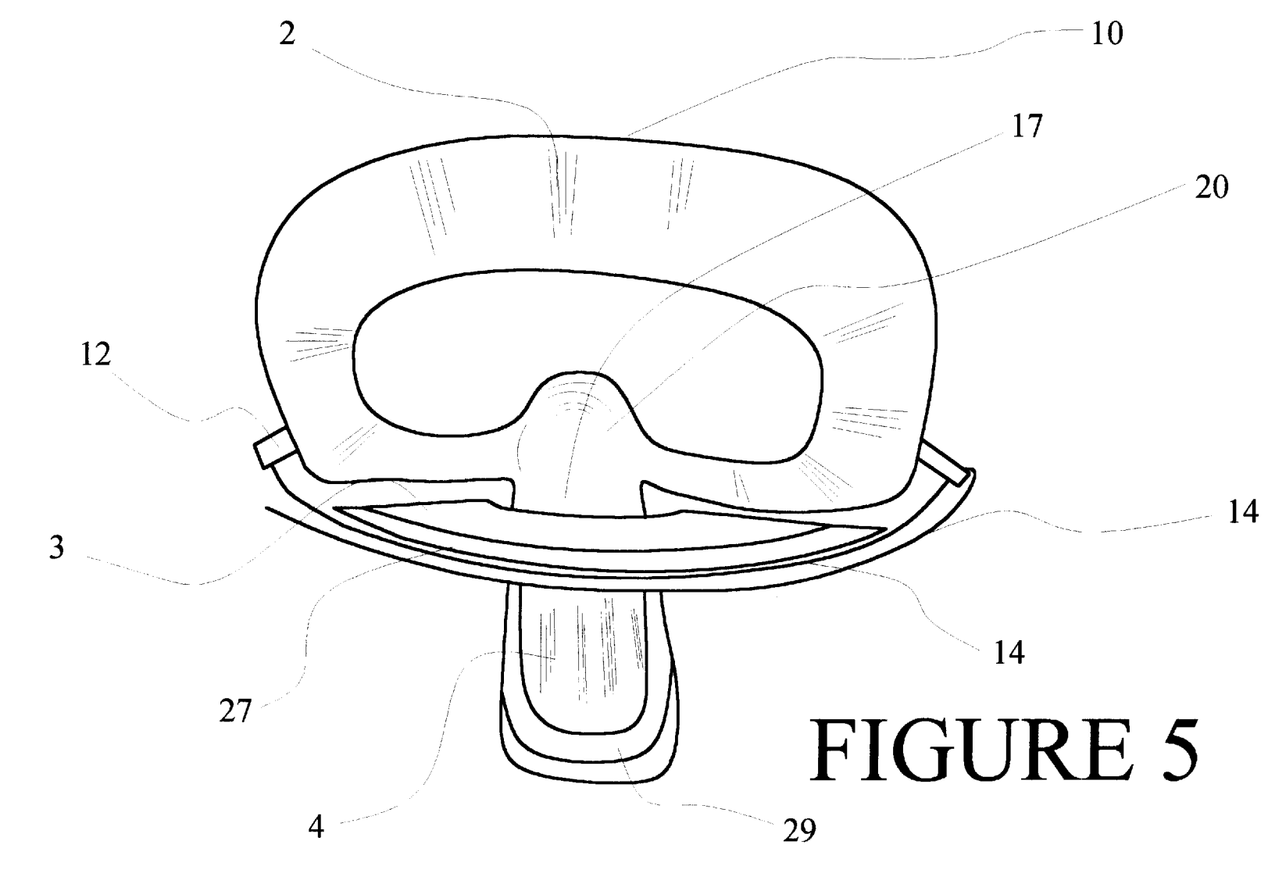
FIG. 5 is a top view of the invention displaying how the straps connect the anterior upper support member to the posterior upper support member.
Figure 6:
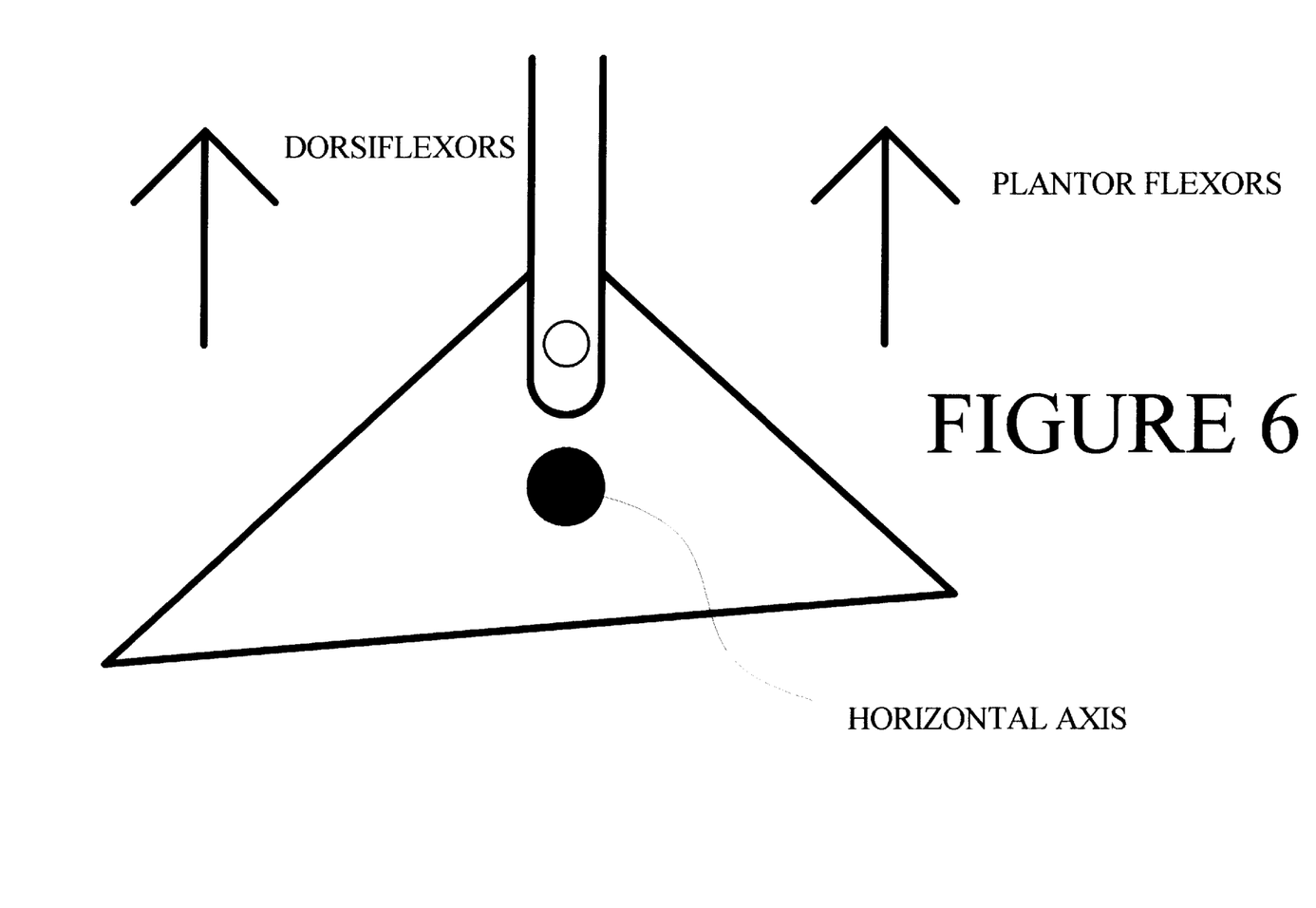
FIG. 6 is an example of dorsiflexor and plantor flexor movements.
Figure 7:
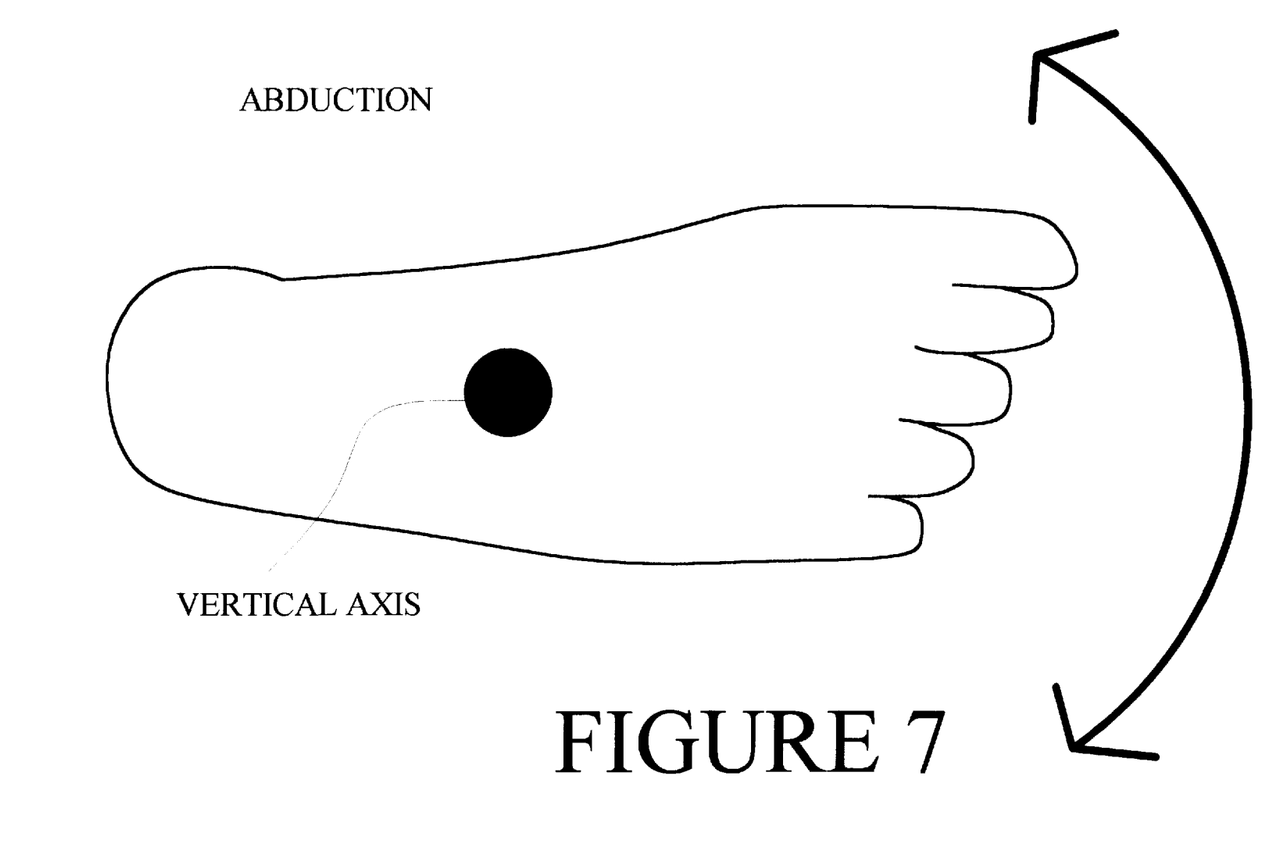
FIG. 7, is an example of abduction and adduction movements.
Figure 8:
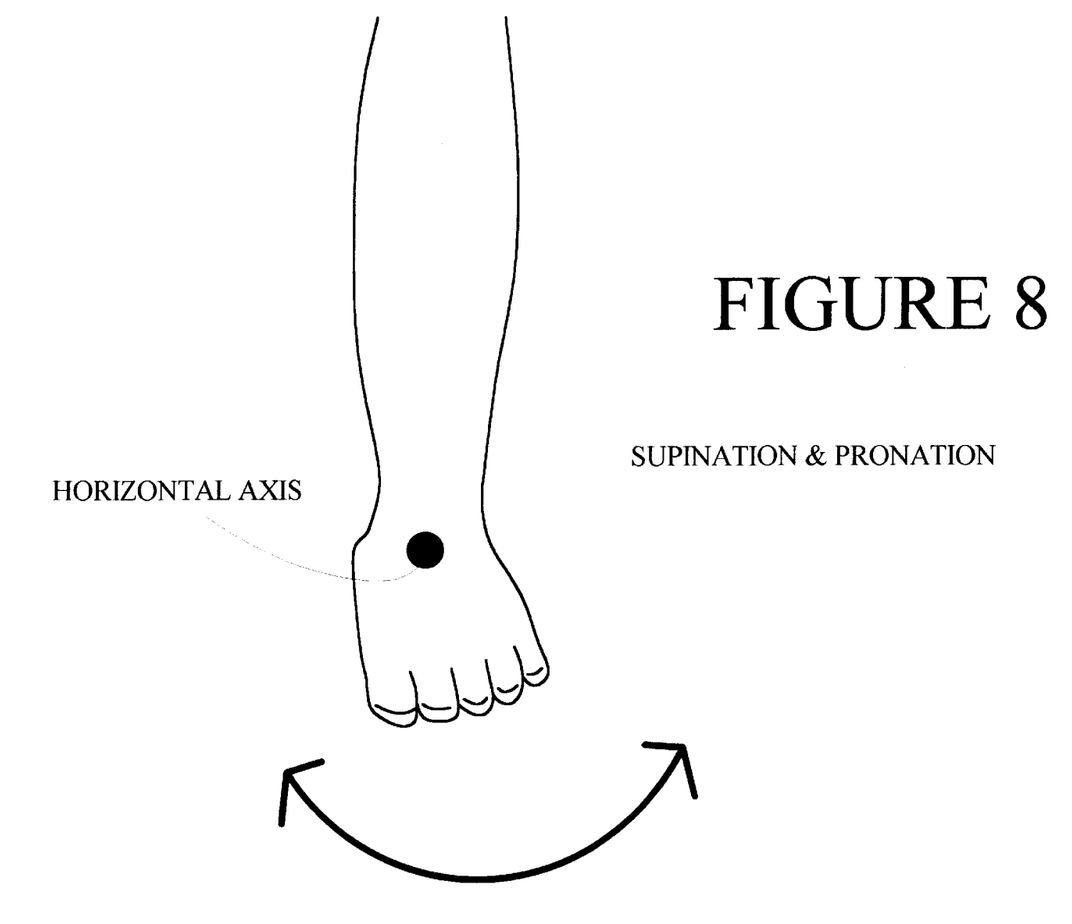
FIG. 8 is an example of movements of supination and pronation.

In carrying out this invention if the illustrative embodiment thereof, a patient opens the strap 14 to expose the front opening 17 or slot. The person then inserts his foot into the opening 17 and slides his leg downwardly until the patient's heel is slid into and abutted against the heel cavity 20 of the foot orthotic 4. The person then places the anterior support member 3 over the front portion of his leg and connects the member 3 to the posterior member 2. The member 3 is connected to member 2 by looping the straps 14 through loops 31 and connecting to itself as shown in FIG. 5.

Accordingly, a very unique, attractive, and convenient apparatus are provided for a lower limb orthotic 1 that aligns and supports the lower limbs of a patient and resist various ankle and foot movements.

Since minor changes and modifications varied to fit particular operating requirements and environments will be understood by those skilled in the art, the invention is not considered limited to the specific examples chosen for purposes of illustration, and includes all changes and modifications which do not constitute a departure from the true spirit and scope of this invention as claimed in the following claims and reasonable equivalents to the claimed elements.

What is claimed is:

1. An improved lower limb orthotic for aligning and supporting a person's lower leg and resisting various ankle and foot movements, said lower limb orthotic comprising:

(a) a pair of lateral supporting members having a substantial elongated construction, said lateral supporting members having an upper, medial, and lower region, said lateral supporting members are placed along the sides of a person's calf muscle;

(b) a foot orthotic having a heel portion, and a front portion, said foot orthotic further having laterally extending walls extending from said heel portion to said front portion, said lateral walls are affixed to the lower region of said lateral supporting members, said foot orthotic further having a composite strip extending from said lateral supporting members across the lower region of said foot orthotic;

(c) a posterior support member affixed to the upper region of said lateral supporting members;

(d) an anterior support member and affixed to said posterior support member.

2. An improved lower limb orthotic for aligning and supporting a person's lower leg and resisting various ankle and foot movements, said lower limb orthotic comprising:

(a) a pair of lateral supporting members having a substantial elongated construction, said lateral supporting members having an upper, medial, and lower region, said lateral supporting members are placed along the sides of a person's calf muscle;

(b) a foot orthotic having a heel portion, and a front portion, said foot orthotic further having laterally extending walls extending from said heel portion to said front portion, said lateral walls are affixed to the lower region of said lateral supporting members, said foot orthotic further having a composite strip extending from said lateral supporting members across the lower region of said foot orthotic;

(c) a posterior support member affixed to the upper region of said lateral supporting members, said posterior support member further having at least one composite strip looped across the posterior support member and affixed to each of the lateral support members; and (d) an anterior support member affixed to said posterior support member.

3. A lower limb orthotic as set forth in claim 2 wherein said composite strip splits into a pair of strips with one strip positioned towards the frontal region, and one strip positioned towards the rear region of said foot orthotic.

4. A lower limb orthotic as set forth in claim 2 wherein said composite strip splits into a pair of strips with one strip positioned towards a top edge and one strip positioned towards a bottom edge of said posterior support member.

* * * * *